(12) United States Patent
Mexis

(10) Patent No.: US 6,562,377 B1
(45) Date of Patent: May 13, 2003

(54) COMPOSITION TO STOP HAIRLOSS

(76) Inventor: George Mexis, 22 Agathoupoleos Str., Athens, Attiki (GR), GR-11252

(*) Notice: Subject to any disclaimer, the term of this patent is extended or adjusted under 35 U.S.C. 154(b) by 0 days.

(21) Appl. No.: 09/381,496

(22) PCT Filed: Jan. 8, 1999

(86) PCT No.: PCT/GR99/00002
§ 371 (c)(1),
(2), (4) Date: Jan. 16, 2001

(87) PCT Pub. No.: WO99/34771
PCT Pub. Date: Jul. 15, 1999

(51) Int. Cl.[7] .................... A61K 35/12; A61K 35/36

(52) U.S. Cl. ....................................... 424/522; 424/574

(58) Field of Search .................. 514/880; 424/70.1, 424/522, 574

(56) References Cited

U.S. PATENT DOCUMENTS

| | | | | |
|---|---|---|---|---|
| 4,139,619 A | * | 2/1979 | Chidsey, III | 424/45 |
| 4,832,946 A | * | 5/1989 | Green | 424/115 |
| 5,116,607 A | * | 5/1992 | Jones | 424/70.14 |

FOREIGN PATENT DOCUMENTS

| | | | |
|---|---|---|---|
| DE | 1792168 A | * | 10/1971 |
| FR | 2167407 A | * | 8/1973 |

* cited by examiner

Primary Examiner—William R. A. Jarvis
Assistant Examiner—Vickie Kim

(57) ABSTRACT

A composition to stop hair-loss and a method of making said composition with a base of paraffin oil, pure alcohol and fur of otters or minks. This composition is oily and is applied on the part of the head which suffers from hair falling. The remaining on the head is 2–3 days without hair washing with shampoos but only with tap water. The hair washing should be done every 7–14 days. The minimum duration of therapy is 2 months.

3 Claims, No Drawings

COMPOSITION TO STOP HAIRLOSS

BACKGROUND OF THE INVENTION

The background of the Invention consists of cosmetic and pharmaceutical methods or mixtures and transplants which all have a way to try to solve the problem of hair loss.

Refering to cosmetic methods or mixtures, they generally use ingredients like menthol and caffeine and others usually in water and some perfume based on sometimes hyperemia of the scalp, others use specific plant extracts.

Referring to pharmaceutical methods or mixtures, they generally use substances like minoxidil, aminexil, cortisone e.t.c. which like side-effects in other therapies they have caused some regrowth and decrease of hair loss or they use anti-andogenic hormones to try to stop the hair loss problem which is generally caused by testosterone.

Refering to transplants, are surgical operations which either use the same person's hair from the back of his head and transplant them in the area which has lost the hair which generally grow or they transplant not natural hair which doesn't grow.

Regarding cosmetic methods or mixtures, so far, they haven't proved that they solve the hair loss problem.

Regarding pharmaceutical methods or mixtures, they temporarily and partially seem to solve the problem but also not in all cases or persons.

Regarding transplants, some of them partially succeed some of them not because not all organisms accept the result of the operations and because they can't cover all the problematic area and also don't stop hair loss.

FIELD OF THE INVENTION

The Invention refers to hair loss (not to pathological ones which are results of sicknesses or chemiotherapies which when persons are cured stops) in men and women of all ages and in every degree of hair loss or baldness.

Hair loss is a problem that occurs mostly in men with several results like small baldness, large baldness, anomiogenic baldness, weak hair, with a tendency to fall, constant hair loss.

Hair loss occurs also in women in a different way of looking and appearance and to explain better the look I enclose pictures showing the degrees of hair loss and baldness called "Androgenetic Alopecia".

Hair loss usually attacks people after the age of $13^{th}$ and continues until the age of about $70^{th}$.

About the Invention to be more specific, it refers to stopping hair loss by:

Firstly, helping the hair and the scalp to regain its healthy nature by ceasing all the dermatological factors like sebum, flakes, redness etc which destroy the healthy nature of the scalp and of the hair, meaning to give back the scalp's and hair's lost natural balance.

Secondly, strengthening and thickening the hair so as not to weaken and fall.

And thirdly, to helping the hair to remain on the head.

BRIEF SUMMARY OF THE INVENTION

The present invention concerns a method of making a composition to stop hair loss obtainable from a mixture comprising paraffin oil, alcohol and a piece of fur from an otter or a mink.

This composition has an oily form and is applied on the part of the head which suffers from hair loss or baldness.

The remaining on the head is 2–3 days without washing with shampoos but only with tap water.

The hair washing should be done every 7 to 14 days depending on the problem.

The minimum duration of the therapy is 2 months.

DETAILED DESCRIPTION OF THE INVENTION (1)

The present invention concerns a method of making a composition to stop hair loss obtainable from a mixture comprising paraffin oil, alcohol and a piece of fur from an otter or a mink, wherein this mixture is placed in a closed plastic vessel for 30 days and a ready for use product is obtained after removing the fur from the vessel. Particularly the present invention concerns a product against hair loss which is a colourless oily liquid and is obtainable from a quantity of paraffin oil which has been used before for making candles, pure alcohol which has been used for pharmaceutical and antiseptic purposes, and one piece of fur of an otter or a mink, both furs are used either for clothing or for preparing cosmetic oils.

So far all the known methods for curing hair loss have an oily form to be used for smearing or are in the state of capsules or pills to be swallowed all which did not reach the wanted results as far as the strengthening of the hair and the appearance of new hair is concerned or they are insufficient concerning their results, or even they are not absorbed by the skin sufficiently so as to perform the rebuilding of the lost hair. For these reasons more and more products appeared on the market.

The purpose of the present invention is to make a soft and gentle product, which is easily absorbed by the pores but also remains longer on the skin and which is a drastic cure for the problem of weak hair which tends to fall out or which has already fallen out. Thus, the present method gives a product obtainable from paraffin oil, alcohol and fur of an otter or a mink as specified herein above.

DE-A-1792168 is directed to compositions for promoting hair growth comprising lyophilisated extracts from the skin of animals with a strong hair growth and parts from nettles. There is no suggestion in D1 to use compositions obtainable by the method of the present invention.

In a preferred embodiment the mixing quantities of the ingredients proportionally are:

1 liter of paraffin oil at room temperature, which is a colourless oily liquid having a density of 0.85 at 20° C. and with a kinematic viscosity of 16.8 mPas (cSt) at 40° C. (low viscosity), 5 drops of pure alcohol, and 1 piece 5×5 cm of fur of an otter or a mink.

As soon as the already mentioned ingredients are placed in a plastic vessel which we close, we shake this mixture well for a well mixed result. The piece of fur remains in the vessel within the mixture for 30 days, then we take it out of the vessel and the product is ready for use.

The final product must be preserved at room temperature.

The qualities of this mixture are:

1. It helps the preservation of the oiliness and the flexibility of the skin of the head, natural qualities, which, with the passing of the time and the senility of the skin gradually disappear. Many of the prior art products against hair loss do not solve this problem. With the smearing of the mixture the pores remain alive, do not close and gradually open If they tend to be dehydrated.

2. It is against the drying of the skin, which is a restraining factor for the hair growth—a phenomen which is reinforced by the often use of several pharmaceutical shampoos.
3. It helps the strengthening of the root of the hair and consequently its strong growth.
4. It reinforces the health and flexibility of the hair.
5. It closes the pores from any damaging factors like the environmental pollution and the weather conditions, something which many existing products against hair loss cannot achieve.

Helping factors for the cure of hair loss during the suggested therapy with the already mentioned mixture are:

a. The avoidance of the daily hair washing (for better and quicker results the hair washing should be done every 7 to 14 days during the therapy), and b. the often or daily use of tap water, as the chlorine that the tap water contains is enough for the daily cleaning of the hair during the period without the use of shampoos which is 7 to 14 days.

The above helping factors are not suggested by several, products of the market which are against hair loss. On the contrary, they suggest often or even daily hair washing, something that affects strongly and weakens the hair.

USE

Place: on the part of the head which suffers from baldness.

Way of using: smearing with massaging backwards.

Duration of remaining the mixture on the head: 2 to 3 days. If nevertheless the hair loss is at a high level, the remaining of the mixture must be increased to double.

DETAILED DESCRIPTION OF THE INVENTION (3)

Example 1

The mixture was used by a person with an already total hair lost 10 years ago on almost all the head area. He smeared the mixture on the hairless part of the head 2–3 times per week. This oily mixture was remained on the head until next hair washing, but where the product had been absorbed, a smearing was made on the part of the head.

During the therapy an often massaging was done upwards.

The first appearance of the new hair was in the form of down, and after a therapy of about 15–20 days.

The down was developed to normal hair after two months therapy.

Example 2

The mixture was used by a person with a hair loss problem in the form of rare hair, particularly much rarer in the front area and at the top of the head as well as at the sides of the head.

The use of this mixture was accomplicated as in the example 1 and with the same result. The important thing is that at the example 2 the hair not only became much richer, but also that the person of that example dyes and also lengthens his hair, especially after the suggested period of the therapy, for 2 years, continuing though the use of the mentioned mixture.

The hair not only stopped falling—even after dying—but it also keeps on becoming stronger and richer.

What is claimed is:

1. A method of making an oily composition for treating hair loss comprising the following steps:

(i). making a mixture by combining paraffin oil, alcohol and a piece of fur from an otter or a mink;

(ii). placing the mixture in a closed plastic vessel for 30 days; and (iii). obtaining a ready for use product after removing the fur from the vessel.

2. The method of claim 1 wherein 1 liter of paraffin oil is mixed with 5 drops of pure alcohol and in which is placed for 30 days a 5×5 cm$^2$ piece of fur of an otter or a mink.

3. An oily composition for topical application comprising paraffin oil, alcohol and a piece of an otter or a mink.

\* \* \* \* \*